US012285297B2

(12) United States Patent
Hoffman (10) Patent No.: US 12,285,297 B2
(45) Date of Patent: Apr. 29, 2025

(54) PERSONAL USE EXTRACORPOREAL LOW INTENSITY SHOCK WAVE DEVICE TIP FORCE DETECTION AND ANNUNCIATION MEANS AND METHODS FOR USING SAME

(71) Applicant: Jonathan Hoffman, Studio City, CA (US)

(72) Inventor: Jonathan Hoffman, Studio City, CA (US)

(73) Assignee: MOON POOL LLC, Chatsworth, CA (US)

( * ) Notice: Subject to any disclaimer, the term of this patent is extended or adjusted under 35 U.S.C. 154(b) by 579 days.

(21) Appl. No.: 16/850,890

(22) Filed: Apr. 16, 2020

(65) Prior Publication Data

US 2021/0219999 A1 Jul. 22, 2021

Related U.S. Application Data

(60) Provisional application No. 62/964,053, filed on Jan. 21, 2020.

(51) Int. Cl.
*A61B 90/00* (2016.01)
*A61B 17/00* (2006.01)
*A61B 17/225* (2006.01)
*A61H 1/00* (2006.01)
*A61H 23/00* (2006.01)
(Continued)

(52) U.S. Cl.
CPC .......... *A61B 90/06* (2016.02); *A61B 17/2251* (2013.01); *A61H 1/006* (2013.01); *A61H 1/008* (2013.01); *A61H 23/004* (2013.01); *A61B 2017/00022* (2013.01); *A61B 2017/0011* (2013.01); *A61B 2017/00119* (2013.01); *A61B 2017/00154* (2013.01); *A61B 2017/927* (2013.01); *A61B 2090/065* (2016.02); *A61H 2023/002* (2013.01); *A61H 2201/5043* (2013.01); *B06B 1/12* (2013.01)

(58) Field of Classification Search
CPC ...... A61B 17/2251; A61B 2017/00022; A61B 2017/0011; A61B 2017/00119; A61B 2017/00154; A61B 2017/927; A61B 90/06; A61B 2090/065; A61H 1/006; A61H 1/008; A61H 23/004; A61H 2023/002; A61H 2201/5043
See application file for complete search history.

(56) References Cited

U.S. PATENT DOCUMENTS 6,217,531 B1  4/2001 Reitmajer
7,390,308 B2  6/2008 Schultheiss
(Continued)

FOREIGN PATENT DOCUMENTS

WO  2007087470 A2  8/2007
WO  2007098300 A2  8/2007

*Primary Examiner* — Chao Sheng
(74) *Attorney, Agent, or Firm* — SLEMAN & LUND LLP (57) ABSTRACT

A tip force monitoring and annunciation means which permits maintaining proper tip pressure during treatment of self-applied acoustic wave treatment for various parts of the user's body by an untrained user. The several embodiments of the disclosure employ designs, materials, and manufacturing methods which are inexpensive and consistent with current manufacturing practices. The functionality, size, cost, simplicity, ease of use, reliability and robustness of the proposed designs are all advantageous.

10 Claims, 5 Drawing Sheets

(51) Int. Cl.
*A61B 17/92* (2006.01)
*B06B 1/12* (2006.01)

(56) References Cited

U.S. PATENT DOCUMENTS

| | | |
|---|---|---|
| 7,470,240 B2 | 12/2008 | Schultheiss et al. |
| 7,497,834 B2 | 3/2009 | Schaden et al. |
| 7,497,835 B2 | 3/2009 | Schultheiss et al. |
| 7,497,836 B2 | 3/2009 | Schultheiss et al. |
| 7,507,213 B2 | 3/2009 | Schultheiss et al. |
| 7,537,572 B2 | 5/2009 | Schultheiss et al. |
| 7,544,171 B2 | 6/2009 | Schaden et al. |
| 7,578,796 B2 | 8/2009 | Schultheiss et al. |
| 7,594,930 B2 | 9/2009 | Warlick et al. |
| 7,600,343 B2 | 10/2009 | Schultheiss et al. |
| 7,601,127 B2 | 10/2009 | Schultheiss et al. |
| 7,695,443 B2 | 4/2010 | Voss |
| 7,775,995 B2 | 8/2010 | Voss |
| 7,841,995 B2 | 11/2010 | Schultheiss et al. |
| 7,883,482 B2 | 2/2011 | Schultheiss et al. |
| 7,905,845 B2 | 3/2011 | Schultheiss et al. |
| 7,988,648 B2 | 8/2011 | Warlick et al. |
| 8,162,859 B2 | 4/2012 | Schultheiss et al. |
| 8,197,444 B1 | 6/2012 | Bazargan et al. |
| 8,257,282 B2 | 9/2012 | Uebelacker et al. |
| 8,535,249 B2 | 9/2013 | Uebelacker et al. |
| 10,716,565 B2 * | 7/2020 | Shelton, IV ........ A61B 17/0682 |
| 2007/0053795 A1 | 3/2007 | Laugharn, Jr. et al. |
| 2007/0239082 A1 | 10/2007 | Schultheiss et al. |
| 2008/0183111 A1 | 7/2008 | Voss |
| 2008/0191596 A1 | 8/2008 | King |
| 2008/0269651 A1 | 10/2008 | Warlick et al. |
| 2009/0041864 A1 | 2/2009 | Warlick |
| 2009/0088670 A1 | 4/2009 | Warlick et al. |
| 2009/0093739 A1 | 4/2009 | Voss |
| 2009/0221940 A1 * | 9/2009 | Marlinghaus ........ A61B 17/225 601/4 |
| 2010/0113966 A1 * | 5/2010 | Spruce .................... A61B 5/00 600/557 |
| 2011/0130714 A1 | 6/2011 | Wells |
| 2011/0177576 A1 | 7/2011 | Schaden et al. |
| 2013/0231735 A1 | 9/2013 | Deem et al. |
| 2014/0350438 A1 | 11/2014 | Papirov et al. |
| 2015/0133950 A1 * | 5/2015 | Shelton ............ A61B 17/22012 606/128 |
| 2016/0022352 A1 | 12/2016 | Johnson et al. |
| 2017/0296185 A1 * | 10/2017 | Swensgard ............ A61B 17/32 |
| 2021/0307845 A1 * | 10/2021 | Park ........................ A61B 5/06 |

* cited by examiner

PERSONAL USE EXTRACORPOREAL LOW INTENSITY SHOCK WAVE DEVICE TIP FORCE DETECTION AND ANNUNCIATION MEANS AND METHODS FOR USING SAME

CROSS-REFERENCE TO RELATED APPLICATIONS

The present application claims the benefit of U.S. Provisional Application Ser. No. 62/964,053, filed Jan. 21, 2020, entitled "PERSONAL USE EXTRACORPOREAL LOW INTENSITY SHOCK WAVE DEVICE TIP FORCE DETECTION AND ANNUNCIATION MEANS," the contents of which are hereby incorporated by reference as if fully set forth herein.

FIELD OF THE DISCLOSURE

The present disclosure relates to tip force detection and annunciation for non-invasive home use medical devices. More specifically, the present disclosure relates to non-invasive home use medical devices utilizing acoustic waves for massage, increasing local blood flow, breaking up plaques in blood vessels, fostering angiogenesis, and cellulite removal.

BACKGROUND OF THE DISCLOSURE

Acoustic wave treatments are well known in the art and have been widely known and used in the professional medical community for several decades. The treatment methodology has been demonstrated to be effective in treating soft tissue injuries or damage, reducing fatty deposits commonly known as cellulite, and most recently for the treatment of male erectile dysfunction.

SUMMARY OF THE DISCLOSURE

In some examples, a treatment device includes a housing having a longitudinal axis extending between a proximal end and a distal end, a striking element disposed within the housing and moveable along the longitudinal axis, a tip disposed adjacent the distal end, the tip having a flange, and a sensor disposed adjacent the flange of the tip.

In some examples, a method of treating tissue includes providing a treatment device including a housing having a longitudinal axis extending between a proximal end and a distal end, a striking element disposed within the housing and moveable along the longitudinal axis, a tip disposed adjacent the distal end, the tip having a flange, and a sensor disposed adjacent the flange of the tip, and gathering data on forces between the tip and the tissue over time via the sensor.

BRIEF DESCRIPTION OF THE DRAWINGS

Various embodiments of the presently disclosed treatment devices are disclosed herein with reference to the drawings, wherein.

Various embodiments of the present disclosure will now be described with reference to the appended drawings. It is to be appreciated that these drawings depict only some embodiments of the disclosure and are therefore not to be considered limiting of its scope.

DETAILED DESCRIPTION OF THE DRAWINGS

Despite the various improvements that have been made to acoustic wave treatment devices, conventional devices suffer from some shortcomings.

There therefore is a need for further improvements to the devices, systems, and methods of manufacturing and using acoustic wave devices, treatment Among other advantages, the present disclosure may address one or more of these needs.

As used herein, the term "proximal," when used in connection with a component of a treatment device, refers to the end of the component farthest from the treatment area, whereas the term "distal," when used in connection with a component of a treatment, refers to the end of the component closest to the treatment area.

Likewise, the terms "trailing" and "leading" are to be taken as relative to the operator of the treatment device. "Trailing" is to be understood as relatively closer to the operator, and "leading" is to be understood as relatively farther away from the operator or closer to the target site of treatment.

In conjunction with the included drawings, this detailed description is intended to impart an understanding of the teachings herein and not to define their metes and bounds. One particular implementation, illustrating aspects of the present teaching, is presented in detail below. Some of the many possible variations and versions are also described.

Generally, electro-mechanical, mechanical, electronic, electro-hydraulic and pneumatic mechanisms may be used to generate an acoustic wave from a device used for extracorporeal acoustic wave treatments. Each of them involves the rapid acceleration of a projectile from an initial state of rest to a maximum velocity at which point it strikes a target whereby an inelastic transfer occurs of the kinetic energy in the accelerated projectile to the target. Since the target is captive and physically constrained, it cannot be displaced but instead generates an acoustic wave. This acoustic wave may then be transferred to any adjacent medium including human tissue. If the target is the tip of the extracorporeal acoustic wave treatment device, and the tip is placed in contact with human tissue, the acoustic signal is transferred to the human tissue. In this manner, the acoustic signal energy, or acoustic wave, is transferred to the human tissue of the subject thereby effecting beneficial medical treatment.

Conventional devices are generally operated by a trained medical professional for treatment of a third-party subject. The efficacy of the treatment is, in part, determined by the pressure with which the tip of the treatment device is held against the target tissue. If the tip pressure is too light, energy transfer is inefficient and treatment benefit will be diminished. If the tip pressure is too great, there is a risk of injury to the tissue. Thus, there may be an optimal range of tip pressure for proper transfer of the acoustic wave energy from the tip of the device to the target tissue.

Given that the device is usually somewhat heavy, is constantly in motion over the target tissue, and is vibrating as a result of the high energy acoustic wave generation mechanism within, it is somewhat difficult for the user to monitor or gauge the tip pressure against their tissue simply by feel. With all known prior acoustic wave treatment devices intended to be operated by professionals and deployed on a third party, it could be relied upon that the trained operator had sufficient knowledge and skill to maintain appropriate tip pressure during treatment. In some cases, costly professional devices monitor and display tip pressure in units which are meaningless to an untrained user, and without value attribution with respect to proper, target, desired, insufficient, or potentially harmful levels and thereby require expert knowledge and interpretation. But in the case of self-treatment by an untrained user, absent a quantifiable measure of tip pressure and clear interpretation of proper and acceptable ranges of tip pressure, it is likely that proper tip pressure will not be easily or consistently maintained throughout a treatment, thereby undermining efficacy of the treatment. It is therefore deemed desirable for there to be an objective means by which tip pressure may be continuously monitored and annunciated to the user to facilitate maintaining proper tip pressure throughout the entirety of the treatment. The means by which this optimal tip pressure is detected and annunciated to the user is the subject of this patent.

While there are presently a number of proposed solutions to the problem of monitoring and annunciating contact pressure of the tip of an acoustic wave device to be applied to an area of the body for soft tissue damage, cellulite reduction, or erectile dysfunction treatment, none has been conceived or implemented to permit a simple, inexpensive, robust, self-use solution which permit self-applied acoustic wave treatment for various parts of the user's body while maintaining proper tip pressure which would be optimal for the application.

Figure 1:
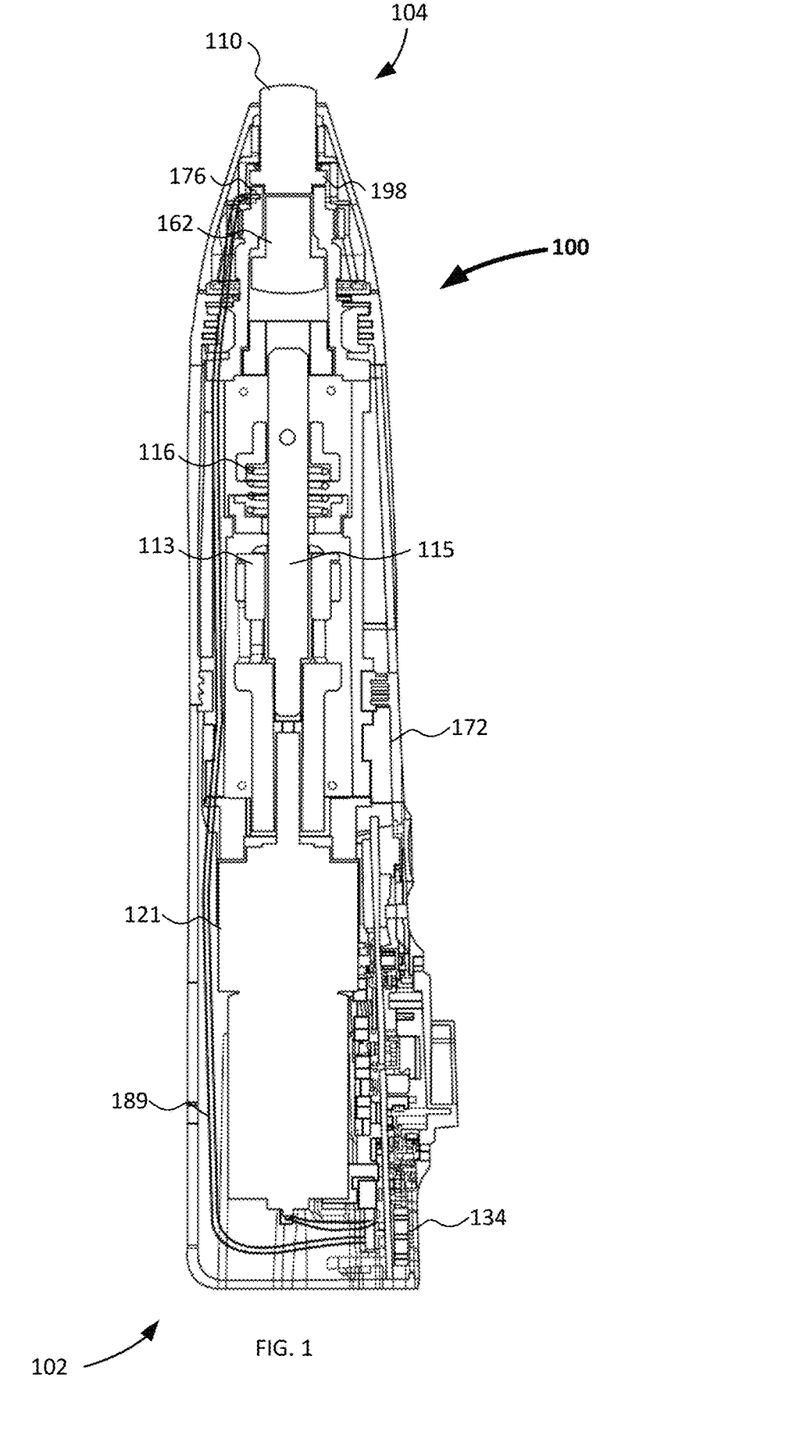
FIG. 1 shows a sectional view of one embodiment of the disclosure illustrating the relative position of major components.

FIG. 1 shows a side sectional view of one embodiment of the device 100 extending between a proximal end 102 and a distal end 104, wherein the general arrangement of major components may be plainly seen including motor 121 which rotates helical cam 113, which causes driveshaft 115 to compress compression spring 116, wherein the stored energy of compressed compression spring 116 is periodically released causing driveshaft 115 to accelerate rapidly forwards and collide with transfer slug 162 which is then accelerated forward to collide with tip 110 thereby imparting an acoustic wave to the user.

Still referring to FIG. 1, it may be seen how force detector 176 is adjacent to, and located behind or rearwards of, the flange 198 on tip 110. In the preferred embodiment, force detector 176 is a piezoelectric load cell, but in other embodiments it may be any of a wide range of force detecting devices or technologies well known in the art including accelerometers or electro-mechanical detectors. The output of force detector 176 is communicated via signal wires 189 to printed circuit board (PCB) assembly 134 where the signals are processed to be displayed to the user.

Figure 2:
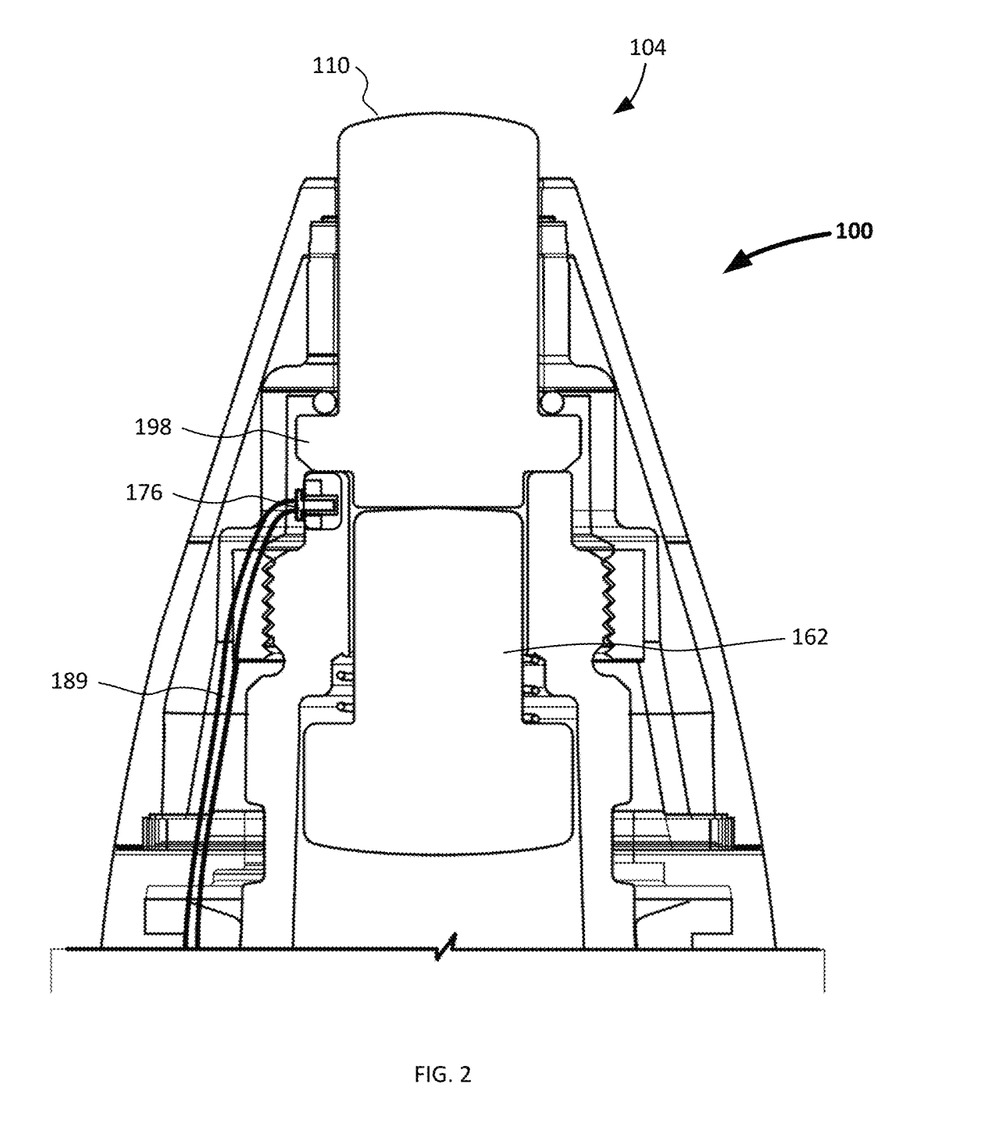
FIG. 2 shows a close-up sectional view of one embodiment of the disclosure with the tip pressure sensor located behind the tip flange.

Referring now to FIG. 2 which is a close-up sectional view of the tip and nose cone assembly of one embodiment of the disclosure, the arrangement of the force detector 176 relative to tip 110 may be plainly seen and the operation of the device may be readily understood. In this view, it may be seen how the force detecting face of force detector 176 rests against the rearward face of tip flange 198 wherein the axis of detection of force detector 176 is aligned with the axis of motion of tip 110 such that when tip 110 is pressed against the user's flesh, this force will be applied to force detector 176, w generates an electrical signal which is communicated to PCB for display to the user.

Still referring to FIG. 2, it may be seen how when transfer slug 162 is accelerated forward to collide with tip 110, the resulting collision with tip 110 produces a tip force in the opposite direction of that generated when tip 110 is pressed against the user's flesh. In the first case, the tip force is generated in a direction away from tip force detector 176 while in the second case, the tip force generated is towards tip force detector 176. Given that these forces are occurring with regular frequency corresponding to the pulse per second operational rate of the device, and given that they occur in opposing directions, the resulting force measurement diagram will approximate a sine wave.

Figure 3:
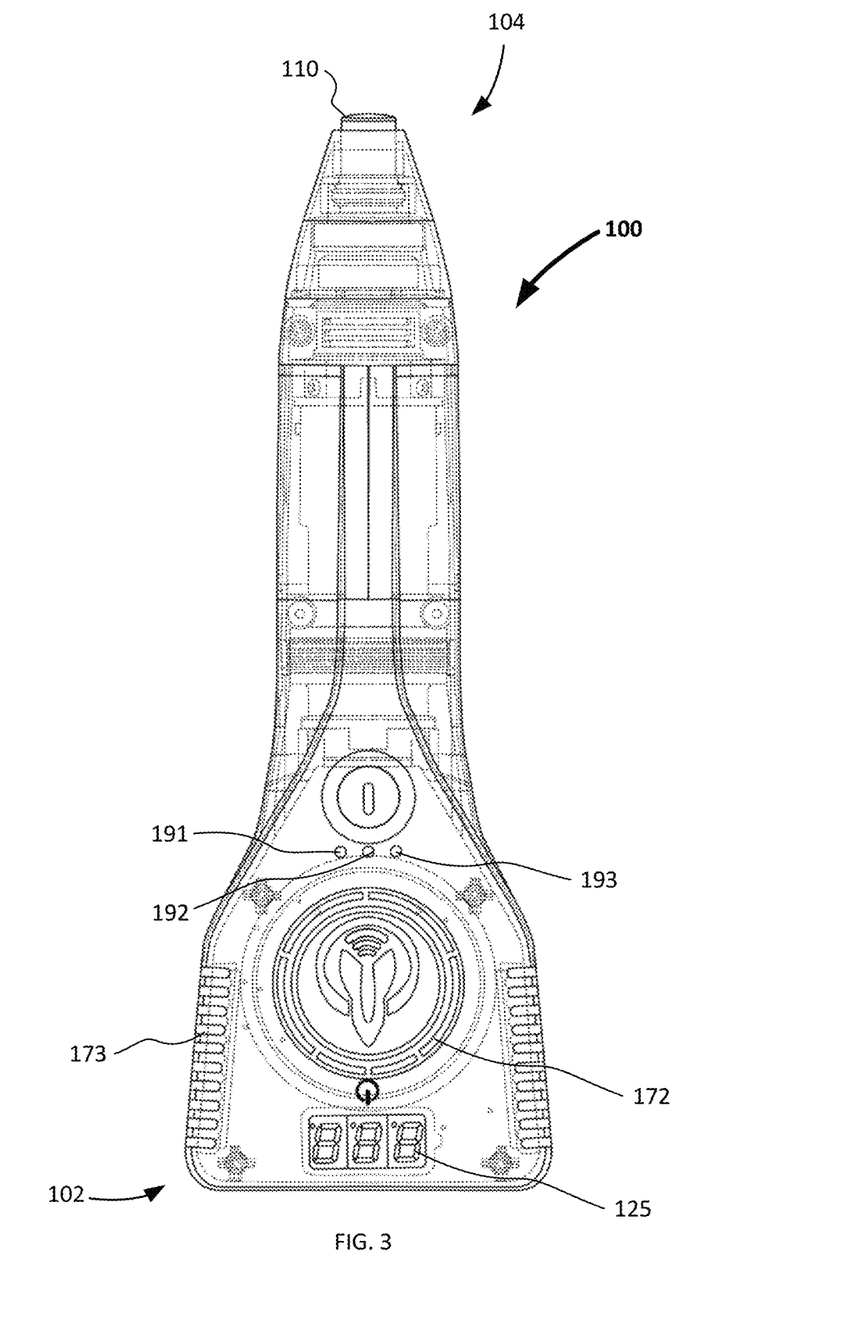
FIG. 3 shows a transparent plan view of one embodiment of the disclosure illustrating the printed circuit board and annunciator LEDs.

Referring now to FIG. 3 which is a transparent plan view of the subject device, it may be seen how annunciator LEDs 191, 192, and 193 are mounted on PCB assembly 134 such that they are visible to the user during operation of the device 100 within view of other critical display annunciators including alphanumeric display 125, bar graph displays 173 and line of travel displays 172.

Figure 4:
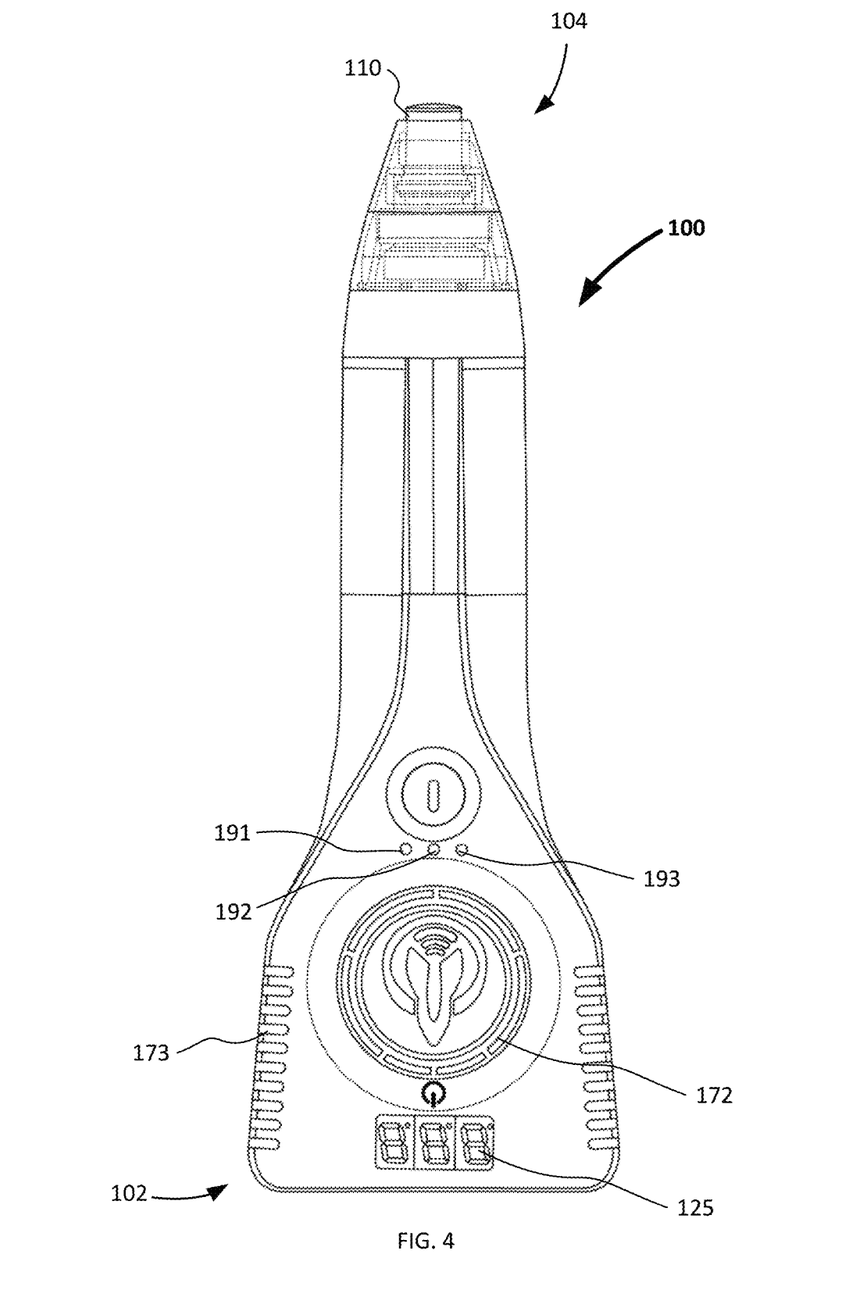
FIGS. 4-5 show three-colored annunciator lights and a representative output graph of a force detection device integrated into the tip of the subject disclosure.
Figure 5:
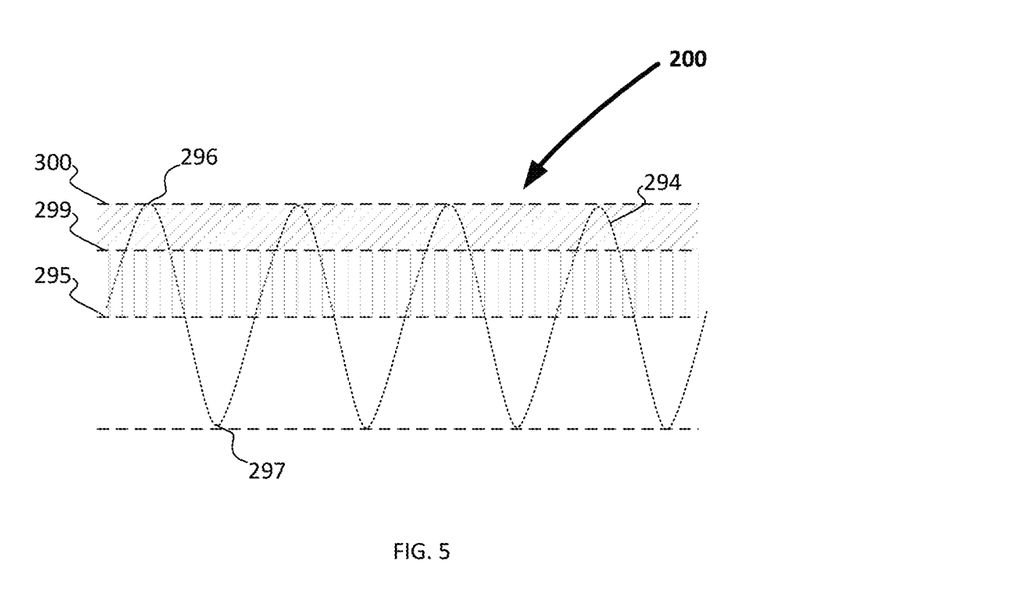

Referring now to FIGS. 4-5 which is a plan view of the device of the subject disclosure and a graphical representation of the tip force experienced by tip force detector 176 during operation, it may be more plainly seen how the opposing forces generated by the impact of transfer slug 162 with tip 110, and the contact of tip 110 with user's flesh will be measured by tip force detector 176.

Still referring to FIG. 5, a graphic representation 200 shows a plurality of thresholds. For example, a horizontal line 295 represents zero force detection by tip force detector 176. Line 295 serves as a baseline reference that represents a condition when tip 110 is not biased from resting position by any external forces—not pressed against user's flesh, and not struck by transfer slug 162. The sinusoidal wave 294 represents the tip force readings measured by tip force detector 176 during operation of the device.

The tip force detector 176 measures the maximum amplitude of the sine wave in each direction, negative (e.g., away from the distal end) and positive (e.g., toward the distal end). In FIG. 5, the maxima of waveform 294 are indicated by a maximum amplitude in a positive direction indicated by peak 296, and a maximum amplitude of the negative direction tip force as indicated by lower peak 297. In some examples, lower peak 297 may not be used, but in another embodiment of the disclosure this data may be used to monitor and quantify the tip force which is of particular value and interest in embodiments of the device where tip force is user adjustable or by some other means variable, such as remotely programmable by a physician or third party.

Still referring to FIG. 5, it may be seen that the amplitude of the positive going tip force is indicated by upper peak 296. This portion of waveform 294 is the target, or desired tip force for optimal device performance and energy transfer to the user's tissue. Line 300 represents a maximum threshold, or a positive going tip force which is excessive and potentially harmful to the user, and line 299 represents a minimum threshold. Three tip force regions are formed with maximum threshold 300 and minimum threshold 299: a region below line 299, a region between line 299 and 300, and a region above line 300, and these regions help determined significant values which the present disclosure quantifies and communicates to the user. Given that tip force detector 176 is subject to a continuously variable sinusoidal force profile by virtue of periodic impacts from transfer slug 162, it may be clearly seen how for purposes of monitoring tip force, only the maximum positive going amplitude of tip force waveform 294 is monitored (e.g., peak 296).

Still referring to FIGS. 4-5, three annunciator lights 191-193 may be used to communicate this data to the user. Colored LEDs are used in the preferred embodiment of the disclosure, but in other embodiments they may be other emissive devices or may be integrated into a display screen and displayed as a bar graph, pie-chart, or some other analog or representative symbol, or voice prompt or sound signal, or haptic signal such as a vibration felt by the user's hand communicate the tip force to the user by indicating which zone, as identified in the preceding paragraph, tip force corresponds to. The annunciator lights are color coded using a 'traffic light' color coding convention well understood by most adults wherein yellow indicated caution, green indicates 'go' and red indicates 'stop.' The color-coding convention used by the device is similar in the yellow indicates inadequate tip force, green indicates proper tip force and red indicates excessive tip force.

If tip force is below the minimum threshold level indicated by line 299 in FIG. 5, for illustrative purposes below 10 pounds per square inch (psi), the yellow annunciator 191 illuminates indicating to the user that inadequate tip force is detected and they must press down on device 100 harder to increase tip force against the tissue. Once detected tip force is within the target range for illustrative purposes between 10 psi and 20 psi, green annunciator 192 illuminates and continues to illuminate while the force within the target region. If tip force exceeds the maximum limit of, for illustrative purposes 20 psi, red annunciator 193 illuminates. It must be noted that the stated pressure values are illustrative only, and actual pressures will be determined based on treatment type and tip characteristics including surface area, material, and profile.

By this means, the user has a simple, color or symbol-based, easy to follow, easy to interpret means of understanding how much tip force they are applying and adjusting it accordingly if it is too little or too much simply by pressing down more or less during operation. This completely eliminates the need to understand or interpret data or force measurements which requires prior knowledge and training as to target values and which is distracting during a self-administered treatment as multiple other displays and actions must be observed and coordinated. Maintaining proper tip force becomes as simple as pressing down on the tip until the green light illuminates and adjusting tip force during use to maintain illumination of the green light. If the green light extinguishes and yellow light illuminates, the user knows to apply more pressure. Conversely, if the green light extinguishes and the red light illuminates, the user knows to back off of tip pressure until the green light illuminates once again. This insures a simple, accurate, constant feedback to maintain ideal tip pressure during use of the device 100. In an alternative embodiment there are only 2 lights-a green light and a red light. There would be no illumination until tip pressure reaches the minimum acceptable threshold at which time a green light would illuminate. If the maximum acceptable threshold is exceeded, the green light would extinguish and the red light would illuminate. These red and green emissive elements may be combined in the same light source such as a bi-color LED. In yet another embodiment, device operation could be inhibited until such time as minimum acceptable tip pressure is achieved, meaning acoustic waves would not be generated and relevant timer and travel rate displays would not be activated until such time as sufficient tip pressure was present.

In broad embodiment, the present disclosure is a simple, inexpensive, and robust, home use solution which permits maintaining proper tip pressure during treatment of self-applied low frequency shock wave treatment for various parts of the user's body by an untrained user. The several embodiments of the disclosure employ designs, materials, and manufacturing methods which are inexpensive and consistent with current manufacturing practices. The functionality, size, cost, simplicity, ease of use, reliability and robustness of the proposed designs are all advantageous.

While the foregoing written description of the disclosure enables one of ordinary skill to make and use what is considered presently to be the best mode thereof, those of ordinary skill will understand and appreciate the existence of variations, combinations, and equivalents of the specific embodiment, method, and examples herein. The disclosure should therefore not be limited by the above described embodiment, method, and examples, but by all embodiments and methods within the scope and spirit of the disclosure as claimed.

The invention claimed is:

1. A treatment device comprising:
a housing having a longitudinal axis extending between a proximal end and a distal end;
a striking element disposed within the housing and moveable along the longitudinal axis;
a tip disposed adjacent the distal end and having a first end and a second end, the first end of the tip being capable of pressing against tissue of the user, and the second end of the tip being strikable by the striking element, the tip having a flange and the tip being axially moveable when struck by the striking element between a first condition in which the tip and the striking element are in contact with one another, and a second condition in which the tip and the striking element are not in contact with one another; and
a sensor disposed adjacent to, and configured to contact, the flange of the tip, the sensor comprising a force detector configured to detect an axial force of the tip pressing against the tissue of the user as the tip oscillates between the first condition and the second condition, the axial force being in line with the longitudinal axis.

2. The treatment device of claim 1, further comprising a printed circuit board and a signal wire coupling the printed circuit board to the sensor.

3. The treatment device of claim 1, wherein the sensor is a piezoelectric load cell axially aligned with an axis of motion of the tip.

4. The treatment device of claim 1, wherein the striking element is a slug.

5. The treatment device of claim 1, further comprising:
a motor disposed within the housing;
a driveshaft operatively coupled to the motor;
a compression spring at least partially disposed about the driveshaft;
a helical cam disposed adjacent the compression spring, the helical cam having a first flat end and a second end having at least one discontinuity.

6. The treatment device of claim 5, wherein the striking element is the driveshaft.

7. The treatment device of claim 1, further comprising a force indicator in communication with the sensor and configured to alert the user when the axial force is too high.

8. The treatment device of claim 7, wherein the force indicator includes a graphical representation of the axial force of the tip against a tissue over time.

9. The treatment device of claim 7, wherein the force indicator includes a plurality of LED lights.

10. The treatment device of claim 9, wherein the plurality of LED lights includes a red light that illuminates when the axial force against a tissue is higher than a maximum threshold, a yellow light that illuminates when the axial force against the tissue is lower than a minimum threshold, and a green light that illuminates when the axial force against the tissue is between the minimum threshold and the maximum threshold.

* * * * *